(12) United States Patent
Anderson

(10) Patent No.: US 9,642,373 B2
(45) Date of Patent: May 9, 2017

(54) INSECTICIDAL COMPOSITIONS AND METHODS OF USING SAME

(71) Applicant: Woodstream Corporation, Lititz, PA (US)

(72) Inventor: David L. Anderson, Lititz, PA (US)

(73) Assignee: WOODSTREAM CORPORATION, Lititz, PA (US)

( * ) Notice: Subject to any disclaimer, the term of this patent is extended or adjusted under 35 U.S.C. 154(b) by 0 days.

(21) Appl. No.: 14/220,215

(22) Filed: Mar. 20, 2014

(65) Prior Publication Data
US 2015/0056312 A1    Feb. 26, 2015

Related U.S. Application Data

(63) Continuation of application No. 11/105,578, filed on Apr. 14, 2005, now abandoned.

(60) Provisional application No. 60/562,252, filed on Apr. 15, 2004.

(51) Int. Cl.
| | | |
|---|---|---|
| A01N 65/26 | (2009.01) | |
| A01N 37/02 | (2006.01) | |
| A01N 53/00 | (2006.01) | |
| A01N 25/02 | (2006.01) | |
| A01N 25/22 | (2006.01) | |
| A01N 25/30 | (2006.01) | |

(52) U.S. Cl.
CPC ............ *A01N 65/26* (2013.01); *A01N 25/02* (2013.01); *A01N 25/22* (2013.01); *A01N 25/30* (2013.01); *A01N 37/02* (2013.01); *A01N 53/00* (2013.01)

(58) Field of Classification Search
CPC ........ A01N 53/00; A01N 25/02; A01N 25/30; A01N 37/02; A01N 2300/00; A01N 27/00; A01N 31/16; A01N 41/02; A01N 49/00; A01N 57/12; A01N 65/00; A01N 25/22; A01N 65/26
USPC ........................................................ 424/761
See application file for complete search history.

(56) References Cited

U.S. PATENT DOCUMENTS

| | | | |
|---|---|---|---|
| 2,087,028 A | | 7/1937 | Gnadinger |
| 2,267,150 A | | 12/1941 | Gnadinger |
| 4,195,080 A | | 3/1980 | Herrera et al. |
| 4,280,999 A | * | 7/1981 | Steelman et al. ............ 514/274 |
| 4,861,762 A | | 8/1989 | Puritch et al. |
| 4,904,645 A | | 2/1990 | Puritch et al. |
| 4,983,591 A | | 1/1991 | Puritch et al. |
| 5,047,424 A | | 9/1991 | Puritch et al. |
| 5,641,480 A | * | 6/1997 | Vermeer .................... 424/70.24 |
| 5,700,473 A | | 12/1997 | Puritch et al. |
| 5,998,484 A | | 12/1999 | Zobitne et al. |
| 6,548,085 B1 | | 4/2003 | Zobitne et al. |
| 6,673,756 B2 | | 1/2004 | Sonnenberg et al. |
| 6,835,719 B2 | * | 12/2004 | Parker ............................. 514/65 |
| 6,849,614 B1 | | 2/2005 | Bessette et al. |
| 2002/0173436 A1 | * | 11/2002 | Sonnenberg ........... C11D 13/14 510/141 |
| 2005/0136089 A1 | | 6/2005 | Bessette et al. |

FOREIGN PATENT DOCUMENTS

| | | |
|---|---|---|
| CA | 2184042 | 11/2003 |
| DE | 3717467 | 12/1988 |
| EP | 0937399 | 8/1999 |
| FR | 2477681 | 8/1980 |
| GB | 2393907 | 4/2004 |
| WO | WO 99/52359 | 10/1999 |
| WO | WO 99/53764 | 10/1999 |
| WO | WO 01/91555 | 12/2001 |
| WO | WO 01/91560 | 12/2001 |
| WO | WO 0191555 A2 * | 12/2001 |
| WO | WO 02/089584 | 11/2002 |

* cited by examiner

*Primary Examiner* — Janet Epps-Smith
*Assistant Examiner* — Courtney Brown
(74) *Attorney, Agent, or Firm* — Jacobson Holman, PLLC.

(57) ABSTRACT

The present invention provides novel insecticidal formulations comprising an effective concentration of: 1) at least one or more essential oils and an insecticidal soap; 2) at least one or more essential oils, an insecticidal soap, and pyrethrins; 3) at least one or more essential oils and pyrethrins; 4) at least one or more essential oils, an insecticidal soap and a synergist, such as sodium lauryl sulfate, sodium dodecyl sulfate or lecithin; 5) at least one or more essential oils, an insecticidal soap, a synergist, and pyrethrins; and 6) at least one or more essential oils, a synergist, and pyrethrins. A carrier oil, such as mineral oil, may be added to any of the foregoing formulations.

19 Claims, 7 Drawing Sheets

Figure 1: Mean Kill Time in Seconds for German Cockroaches.

| Mint Oil | 3% Lecithin | Pyrethrin + 3% Lecithin | | | Potassium Salts of Fatty Acids | | | 0.012% Pyrethrin + 1.0% Potassium Salts of Fatty Acids | 0.05% Pyrethrin + 1.0% Potassium Salts of Fatty Acids | 0.05% Pyrethrin + 2.0% Potassium Salts of Fatty Acids | 0.012% Pyrethrin + 1% SLS | 0.05% Pyrethrin + 1% SLS | 0.1% Pyrethrin + 1% SLS |
|---|---|---|---|---|---|---|---|---|---|---|---|---|---|
| | 0% | 0.012% | 0.05% | 0.10% | 0.50% | 1% | 2% | | | | | | |
| 0% | 300 | 268.53 | 269.57 | 273.68 | 132.54 | 97.273 | 139.01 | 172.73 | 142.25 | 128.88 | 260.64 | 276.17 | 300 |
| 0.25% | 223.85 | 269.95 | 270.69 | 281.77 | 107.22 | 102.41 | 79.467 | 98.407 | 54.313 | 54.273 | 255.2 | 278.97 | 265.39 |
| 1.00% | 192.62 | 252.45 | 192.69 | 205.32 | 74.133 | 79.147 | 60.947 | 85.1 | 46.927 | 70.693 | 253.61 | 253.42 | 195.66 |
| 4.00% | 108.57 | 169.31 | 156.37 | 94.833 | 92.5 | 73.08 | 54.707 | 110.61 | 58.473 | 45.613 | 87.92 | 136.33 | 100.85 |

Figure 2: Mean Kill Time in Seconds for Carpenter Ants.

| Essential Oil | Water | 3% Lecithin | 0.012% Pyrethrin | 0.05% Pyrethrin + 3% Lecithin | 0.50% Potassium Salts of Fatty Acids | 1% Potassium Salts of Fatty Acids | 0.012% Pyrethrin + 1.0% Potassium Salts of Fatty Acids | 0.05% Pyrethrin + 1.0% Potassium Salts of Fatty Acids | 0.012% Pyrethrin + 1% SLS | 0.05% Pyrethrin + 1% SLS |
|---|---|---|---|---|---|---|---|---|---|---|
| 0% Oil | 300 | 181.45 | 148.86 | 78.53 | 61.716 | 46.49 | 54.43 | 49.198 | 158.26 | 105 |
| 0.25% Mint Oil | 300 | 55.822 | 54.744 | 53.89 | 52.802 | 53.314 | 39.03 | 48.07 | 210.88 | 84.43 |
| 1% Mint Oil | 300 | 38.556 | 40.498 | 47.488 | 39.746 | 40.144 | 38.7 | 48.682 | 46.044 | 119.3 |
| 0.25% D-Limonene | 300 | 49.376 | 88.364 | 64.592 | 50.676 | 60.476 | 39.036 | 36.494 | 207.67 | 260.18 |
| 1% D-Limonene | 275.64 | 50.437 | 41.866 | 48.764 | 62.026 | 45.082 | 47.744 | 38.228 | 115.21 | 90.59 |
| 0.25% Palmarosa Oil | 272.06 | 36.066 | 36.996 | 34.724 | 33.864 | 32.808 | 38.14 | 32.234 | 55.094 | 36.894 |
| 1% Palmarosa Oil | 265.37 | 33.788 | 34.762 | 31.156 | 36.15 | 31.76 | 30.94 | 29.256 | 24.498 | 31.53 |

Figure 3: Mean Kill Time in Seconds for German Cockroaches.

| Eugenol | 3% Lecithin | Pyrethrin + 3% Lecithin | | | | Potassium Salts of Fatty Acids | | | 0.012% Pyrethrin + 1.0% Potassium Salts of Fatty Acids | 0.025% Pyrethrin + 1.0% Potassium Salts of Fatty Acids | 0.05% Pyrethrin + 2.0% Potassium Salts of Fatty Acids | 0.012% Pyrethrin + 1% SLS | 0.025% Pyrethrin + 1% SLS | 0.05% Pyrethrin + 1% SLS | 0.1% Pyrethrin + 1% SLS |
|---|---|---|---|---|---|---|---|---|---|---|---|---|---|---|---|
| | 0% | 0.012% | 0.05% | 0.10% | 0.50% | 1% | 2% | | | | | | | |
| 0% | 300 | 258.53 | 269.57 | 273.68 | 132.54 | 97.273 | 130.01 | 172.73 | 142.25 | 128.98 | 260.6 | 276.17 | 300 |
| 0.25% | 286.7 | 288.37 | 286.79 | 275.64 | 117.46 | 143.67 | 199.47 | 103.52 | 51.3 | 78.247 | 283.37 | 300 | 300 |
| 1.00% | 277.59 AB | 273.63 | 264.17 | 191.53 | 91.307 | 100.72 | 80.2 | 92.857 | 51.78 | 69.34 | 296.69 | 300 | 285.35 |
| 4.00% | 246.55 B-D | 202.53 | 212.09 | 166.63 | 73.569 | 112.11 | 149.96 | 86.347 | 35.967 | 84.54 | 149.38 | 200.47 | 141.94 |

Figure 4: Mean Kill Time in Seconds for German Cockroaches.

| THYME | 3% Lecithin | Pyrethrin + 3% Lecithin | | | Potassium Salts of Fatty Acids | | | 0.012% Pyrethrin + 1.0% Potassium Salts of Fatty Acids | 0.05% Pyrethrin + 1.0% Potassium Salts of Fatty Acids | 0.05% Pyrethrin + 2.0% Potassium Salts of Fatty Acids | 0.012% Pyrethrin + 1% SLS | 0.05% Pyrethrin + 1% SLS | 0.1% Pyrethrin + 1% SLS |
|---|---|---|---|---|---|---|---|---|---|---|---|---|---|
|  | 0% | 0.012% | 0.05% | 0.12% | 0.50% | 1% | 2% |  |  |  |  |  |  |
| 0% | 300 | 283.53 | 283.57 | 273.88 | 132.54 | 97.273 | 130.01 | 172.73 | 142.25 | 128.98 | 280.6 | 276.2 | 300 |
| 0.25% | 267.13 | 300 | 300 | 250.26 | 128.59 | 118.69 | 73.76 | 125.15 | 51.653 | 40.347 | 223.65 | 300 | 283.18 |
| 1.00% | 280.06 | 230.68 | 234.27 | 225.27 | 114.93 | 69.187 | 57.007 | 61.287 | 58.7 | 94.073 | 286.96 | 300 | 282.23 |
| 4.00% | 203.77 | 169.34 | 115.95 | 105.57 | 64.9 | 44.847 | 37.747 | 120.5 | 60.593 | 45.18 | 196.5 | 157.35 | 248.73 |

Figure 5: Mean Kill Time in Seconds for German Cockroaches.

| Essential Oil | D-Water 0% | 3% Lecithin 0% | Pyrethrin 0.012% | Pyrethrin + 3% Lecithin 0.05% | Insect Killing Soap 0.50% | Insect Killing Soap 1% | 0.012% Py + 1.0% Soap | 0.05% Py + 1.0% Soap | 0.05% Py + 0.012% Py 1% SLS | 0.05% Py 1% SLS |
|---|---|---|---|---|---|---|---|---|---|---|
| 0% No Oil | 300 | 106.6 | 87.334 | 79.358 | 72.286 | 74.74 | 53.22 | 45.048 | 198.5 | 98.856 |
| 0.25% Mint | 225.47 | 82.074 | 79.844 | 70.318 | 70.052 | 97.216 | 67.138 | 61.412 | 145.58 | 73.5 |
| 1% Mint | 121.83 | 55.656 | 74.834 | 63.18 | 61.322 | 51.698 | 56.268 | 55.896 | 85.482 | 61.17 |
| 0.25% D-limonene | 178.57 | 69.182 | 120.41 | 64.016 | 64.79 | 78.446 | 50.204 | 72.27 | 99.768 | 62.832 |
| 1% D-limonene | 70.114 | 90.75 | 108.58 | 49.662 | 64.71 | 67.286 | 52.518 | 55.548 | 75.806 | 63.886 |
| 0.25% Palmarosa | 102.39 | 79.854 | 72.748 | 71.756 | 59.44 | 57.63 | 48.73 | 44.41 | 101.3 | 73.814 |
| 1% Palmarosa | 94.062 | 84.976 | 71.382 | 77.624 | 45.956 | 45.454 | 45.496 | 44.042 | 65.708 | 49.58 |

Figure 6: Mean Kill Time in Seconds for Carpenter Ants.

| Essential Oil | 0.012% Py + 1.0% Soap | 0.05% Py + 1.0% Soap | 0.05% Py 2.0% Soap |
|---|---|---|---|
| 0% Oil Control | 74.553 | 66.58 | 51.673 |
| 0.25% Mint | 41.427 | 31.213 | 44.613 |
| 1% Mint | 82.88 | 25.053 | 25.92 |
| 4% Mint | 175.28 | 26.14 | 21.473 |
| 0.25% D-Limonene | 104.18 | 19 | 27.447 |
| 1% D-Limonene | 70.933 | 16.518 | 39.38 |
| 4% D-Limonene | 43.24 | 18.933 | 33.453 |
| 0.25% Thyme Oil | 139.27 | 62.8 | 65.047 |
| 1% Thyme Oil | 86.673 | 53.22 | 52.267 |
| 4% Thyme Oil | 189.21 | 82.587 | 121.37 |
| 0.25% Eugenol | 114.86 | 59.813 | 79.393 |
| 1% Eugenol | 112.18 | 99.553 | 128.36 |
| 4% Eugenol | 213.07 | 82.613 | 144.62 |
| 0.25% Cedar Oil | 64.193 | 48.493 | 46.807 |
| 1% Cedar Oil | 60.787 | 59.667 | 38.247 |
| 4% Cedar Oil | 106.33 | 47.06 | 58.627 |
| 0.25% Cinnamon Oil | 59.007 | 41.28 | 55.74 |
| 1% Cinnamon Oil | 75.427 | 56.94 | 51.027 |
| 4% Cinnamon Oil | 198.25 | 79.053 | 92.16 |
| 0.25% Neem Oil | 73.647 | 30.14 | 31.32 |
| 1% Neem Oil | 34.72 | 55.5 | 52.287 |
| 4% Neem Oil | 45.54 | 82.953 | 24.913 |
| 0.25% Geraniol | 56.553 | 29.7 | 29.333 |
| 1% Geraniol | 54.54 | 32.247 | 31.62 |
| 4% Geraniol | 43.6 | 51.927 | 25.14 |

Figure 7: Mean Kill Time in Seconds for German Cockroaches.

|  | 3% Lecithin | Pyrethrin + 3% Lecithin | | | Potassium Salts of Fatty Acids | | | 0.012% Pyrethrin + 1.0% Potassium Salts of Fatty Acids | 0.05% Pyrethrin + 1.0% Potassium Salts of Fatty Acids | 0.05% Pyrethrin + 2.0% Potassium Salts of Fatty Acids | 0.012% Pyrethrin + 1% SLS | 0.05% Pyrethrin + 1% SLS | 0.1% Pyrethrin + 1% SLS |
|---|---|---|---|---|---|---|---|---|---|---|---|---|---|
| D-Limonene | 0% | 0.012% | 0.05% | 0.10% | 0.50% | 1% | 2% | | | | | | |
| 0% | 300 | 258.53 | 269.57 | 273.65 | 132.54 | 97.273 | 130.01 | 172.73 | 142.25 | 123.98 | 260.6 | 276.2 | 300 |
| 0.25% | 220.99 | 259.74 | 266.45 | 252.13 | 221.05 | 86.367 | 63.573 | 86.9 | 93.033 | 77.76 | 290.23 | 300 | 283.21 |
| 1.00% | 222.94 | 276.13 | 259.77 | 223.64 | 134.95 | 88.747 | 54.36 | 101 | 41.513 | 67.673 | 285.26 | 280.4 | 232.5 |
| 4.00% | 34.247 M-O | 243.11 | 159.23 | 122.64 | 161.78 | 96.18 | 50.107 | 63.957 | 57.367 | 48.427 | 228.61 | 161.79 | 142.69 |

ND METHODS OF USING SAME

INSECTICIDAL COMPOSITIONS AND METHODS OF USING SAME

RELATED APPLICATION

This is a continuation of application Ser. No. 11/105,578, filed Apr. 14, 2005, which claims the benefit of U.S. Provisional Application No. 60/562,252, filed Apr. 15, 2004, the disclosures of which are incorporated herein by reference.

BACKGROUND OF THE INVENTION

1. Field of Invention

This invention relates generally to insecticidal compositions and methods of using same to control various crawling and flying insect pests, and, in its preferred embodiments, relates more particularly to a combination of synergistic non-poison insecticides by themselves and in combination with a known poison insecticide at a greatly reduced concentration, and adapted to unexpectedly increase insect mortality and reduce kill time.

2. Description of Prior Art

Commercially available insecticides, including those available for home use, commonly comprise active ingredients or poisons which are not only toxic to the target insect pests, but, if used in relatively confined environments and delivered as aerosol sprays, can be present in sufficient concentration to also be toxic to humans and household pet. Various undesirable side effects may include immediate or delayed neurotoxic reactions, and/or suffocation. Even the noxious odor of such materials can cause headaches or upset stomachs in some individuals. These adverse side effects are exacerbated when such compositions come in contact with persons of increased sensitivity, or persons of small body mass such as children or babies.

For some time, efforts have been made to develop insecticidal compositions, particularly, those intended for residential use in aerosol form, which are effective in killing the targeted insect pests completely and quickly, but non-toxic to humans and pets. The Environmental Protection Agency (EPA) regulates the use of potentially toxic ingredients in pesticidal compositions under the Federal Insecticide, Fungicide and Rodenticide Act (FIFRA). Certain materials considered to be either active or inert materials by the EPA have been deregulated or otherwise identified as acceptable safe substances under FIFRA offering minimum risk in normal use. Other materials are currently undergoing investigation and may be deregulated in due course. Consumers generally consider deregulated substances non-poisonous. Thus, the term non-poisonous as used herein is intended to convey a compound or composition that, while highly effective in killing targeted insect pests, is safe to use around humans, particularly small children, and pets.

Among the insects that are found to be particularly undesirable are cockroaches, both the American and German species. These pests shed their skin, which, over time, disintegrates forming what is known as cuticle in the air, a particular problem for people suffering from asthma. Thus, not only is it important to kill cockroaches with an effective insecticide, but also the kill time must be sufficiently short for the carcass to be properly disposed of before the insect can crawl into a remote area to die.

While cockroaches are a prime target for a household spray, for general application such materials must also be effective against other crawling insects, such as ants, water bugs, silverfish, crickets, spiders and centipedes. Additionally, aerosol compositions of such insecticides of proper concentration must also be effective against various flying insects, including flies, mosquitoes, gnats, moths, wasps, hornets, yellow jackets and other bees, both inside and outside of the house.

One of the materials exempted by the EPA under FIFRA is cornmint oil (also known as Japanese mint or *Mentha arvensis*). Cornmint oil includes a high concentration of menthol and is known to contain alpha-pinene, myrcene, limonene, gamma-terpenine, 3-octanol, menthofuran, beta-caryophyllene, germa-crene D and beta-pinene, along with other components. As with other mint oils, cornmint oil has been used as a flavoring agent in mouthwashes, cough syrups, throat lozenges, chewing gum, and the like.

Recently, it has been found that when cornmint oil was combined with a synergist such as sodium lauryl sulfate ("SLS"), cornmint oil became a highly effective insecticide against common household pests such as American and German cockroaches and black ants. These findings are described in U.S. Pat. No. 5,998,484 (the "'484 patent"), assigned to Woodstream Corporation. These findings were surprising because prior to the '484 patent, cornmint oil had not been shown to be particularly effective, and certainly was not distinguished from other materials of this kind as a candidate for special attention.

Other essential oils currently deregulated by the EPA under FIFRA include cedar oil, cinnamon oil, citronella oil, clove oil, corn oil, garlic oil, lemongrass oil, linseed oil, peppermint oil, rosemary oil, soybean oil and thyme oil. Among the essential oils proposed for exemption from registration are a number of the citrus oils. Citrus oils would include orange oil, lemon oil, lime oil, grapefruit oil and tangerine oil.

As with cornmint oil, it was also recently discovered that many of these other deregulated essential oils which had not been previously shown to be particularly effective as active ingredients, by themselves, were in fact effective insecticidal compositions when combined with a synergist such as lecithin or SLS. These insecticidal compositions can be found in U.S. Pat. No. 6,548,085, also assigned to Woodstream Corporation.

Pyrethrum is a natural plant oil that occurs in the Pyrethrum daisy, *Tanacetum cinerariaefolium*, a member of the chrysanthemum family (*Chrysanthemum cinerariaefolium*). It is found mainly in tiny oil-containing glands on the surface of the seed case in the tightly packed flower head. Pyrethrum flowers are also known as Dalmatian Insect powder and Persian Insect powder. Several trade names associated with these compounds are Buhach, *Chrysanthemum Cinerariaefolium*, Ofirmotox, Insect Powder, Dalmation Insect Flowers, Firmotox, Parexan and NA 9184. The flowers of the plant are harvested shortly after blooming and are either dried and powdered or the oils within the flowers are extracted with solvents. The resulting mixture of pyrethrin containing dusts and extracts usually have an active ingredient content of about 30%. These active insecticidal components of pyrethrum are collectively known as pyrethrins. Two pyrethrins are most prominent, pyrethrin-I and pyrethrin-II. The pyrethrins include other active ingredients such as Cinerin I and II, Jasmolin I and II, pyrethrosin, pyretol, pyrethrotoxic acid, chrysanthemine, chrysanthemumic acid. See, Merck Index, Eleventh ed., (1989).

Pyrethrin compounds have been used primarily to control human lice, mosquitoes, cockroaches, beetles and flies. Some "pyrethrin dusts," used to control insects in horticultural crops, are only 0.3% to 0.5% pyrethrins, and are used at rates of up to 50 lb/Acre. Other pyrethrin compounds may be used in grain storage and in poultry pens and on dogs and cats to control lice and fleas. However, the natural pyrethrins are contact poisons which quickly penetrate the nervous system of the insect. A few minutes after application, the insect cannot move or fly away. The natural pyrethrins can be swiftly detoxified by enzymes in the insect. Semisynthetic derivatives of the chrysanthemumic acids have been developed as insecticides. These are called pyrethroids and tend to be more effective than natural pyrethrins while they are less toxic to mammals. One common synthetic group of pyrethroid compounds are the allethrins, also known as allyl cinerins (allethrin I and II).

Pyrethrum was used commercially many years ago as an insecticide, primarily in the form of "oleoresin of pyrethrum". Oleoresin of pyrethrum is an archaic pharmaceutical term for an ether extract of the cinerariaefolium variety of chrysanthemum. It contains volatile oils and components having insecticidal properties, called pyrethrins, jasmolins, and cinerins. These materials are known to be toxic to insects, essentially non-toxic to mammals, to lack persistence in the environment, and to be characterized by negligible biological magnification in the food chain.

As used herein, the term "pyrethrins" is intended to mean pyrethrin and its active components. One of the problems with using pyrethrins as insecticides is their high cost per unit dose. An example of such a composition comprising a mixture of saponified organic acids, i.e., salts of coconut oil, and pyrethrins was sold commercially under the trademark Red Arrow about 55 years ago. However, these mixtures did not solve the expense problem because of their high pyrethrin content, about 40% by weight, and because the coconut oil soaps contributed little to their insecticidal efficacy. In fact, most commercially available fatty acid soap compositions contain an excess of alkali which is thought to promotes hydrolysis and inactivation of pyrethrins. Pyrethrin-based insecticides also degrade rapidly in storage and in use.

More recently, the commercially effective use of pyrethrins was shown when pyrethrins were combined with certain fatty acid salts and a low molecular weight alcohol, such as isopropanol. See for example, U.S. Pat. Nos. 4,904,645, and 4,983,591.

Insect killing soap has also been sold commercially as an insecticide for many years. An example is the Safer® Brand Insect Killing Soap Formulation. This insecticide soap formulation contains about 49.52% potassium salts of fatty acids by weight, and was used to formulate treatments containing about 1.0% to about 2.0% potassium salts of fatty acids by weight. Insecticidal soap has also been shown to have synergistic effects when combined with an insecticide, i.e. pyrethrin, and the soap and compositions of soap and pyrethrins are described in U.S. Pat. Nos. 4,861,762, 4,983,591 and 5,047,424. These three patents, as well as U.S. Pat. Nos. 6,548,085, and 5,998,484 which describe the combination of essential oils and a synergist, are all incorporated by reference herein as if fully set forth in their entireties.

SUMMARY OF THE INVENTION

In accordance with the present invention, it has now been found that insecticidal soap, when combined with one or more essential oils, has a similar effect on killing insects as synergists such as SLS, thus resulting in a more efficacious product. Further, by combining appropriate concentrations of insecticidal soap and at least one essential oil, it has been found that a lower concentration of each individual component is needed than if they were used separately. In addition, insecticidal soap by itself, has poor efficacy on hard bodied insects (i.e. beetles), and the combination of an essential oil and soap provides a novel formulation that is able to control a broader range of insects.

Essential oils which are useful in the present invention include cornmint (mint) oil, cedar oil, cinnamon oil, citronella oil, clove oil, corn oil, garlic oil, lemongrass oil, linseed oil, peppermint oil, rosemary oil, soybean oil, citrus oils such as orange oil, lemon oil, lime oil, grapefruit oil and tangerine oil, neem oil, thyme oil, eugenol, geraniol, palmarosa oil, and D-limonene.

Any suitable insecticidal soap could be used in the compositions of the present invention. One insecticidal soap known to be useful in accordance with the present invention is SAFER® Brand Insect Killing Soap Concentrate, which is marketed by Woodstream Corporation, of Lititz, Pa., the assignee of the present application. This soap concentrate comprises 43.96% Emersol 213 (Oleic Acid), 5.56% potassium hydroxide, 35.61% denatured alcohol (SD3A or SDA 3C), and 14.87% water. Other commercially available insecticidal soaps having the same or similar ingredients could also be used in the compositions of the present invention.

While not intending to be bound by any particular theory for the present invention, it is believed that efficacy of the insecticidal soap operates to kill insects by removing the waxy layer covering their bodies resulting in dehydration and ultimately death. Soap will also cause the rupturing of cell membranes and disrupt the cellular osmotic relationships. Essential oils, in contrast, work by attacking the nervous system of insects, but must first penetrate the waxy layer covering the insect. It has now been found that when at least one essential oil and insecticidal soap are combined, insecticidal efficacy is improved. It is believed that the combination has a synergistic effect in that the soap solubilizes the waxy outer layer of the insect and weakens the cell membranes, thereby allowing the essential oil to penetrate the exoskeleton and reach the insect's nervous system more quickly.

In an alternate embodiment, the present invention provides a synergistic composition comprising insecticidal soap, at least one essential oil, and pyrethrins. Any suitable pyrethrin concentrate can be used in the foregoing synergistic composition. Pyrethrin concentrates typically include an antioxidant such as ethoxyquin, a tocopherol, or BHT to prevent the pyrethrins from breaking down. Further, since pyrethrins are not readily soluble in water, an alcohol may also be included, such as SD3A or SDA 3C, or other denatured alcohols, to help solubilize the pyrethrins. By combining appropriate concentrations of the insecticidal soap, one or more essential oils and pyrethrins, lower concentrations of the individual components are needed than if they were used separately, thereby lowering overall toxicity to humans and pets.

It is a primary object of the instant invention to provide a non-poisonous broad-spectrum insecticide containing, as an essential active ingredient, materials that have been approved by the EPA as safe or as offering minimum risk in products of this nature. Consistent with this objective, this invention provides an aerosol insecticide which is not detrimental to the health of humans or pets and which is environmentally safe, yet effective in killing targeted insect pests with which it comes in contact.

Another object of the instant invention is the provision of an insecticidal composition that not only effectively kills 100% of the targeted insects with which it comes in contact, but kills such insects within seconds of contact so that the user can be certain of the effectiveness of the insecticide, and the insect carcass can be safely and easily disposed of without contaminating the environment.

Yet a further object of this invention is the provision of an insecticidal composition comprising a combination of ingredients which individually are relatively ineffective, but act in concert to provide high total killing power with a substantially decreased kill time.

Yet another object of this invention is the provision of an insecticidal composition comprising one or more essential oils, preferably selected from the group consisting of cedar oil, cornmint oil, cinnamon oil, citronella oil, lemongrass oil, peppermint oil, orange oil, lemon oil, lime oil, grapefruit oil, tangerine oil, neem oil, thyme oil, eugenol, geraniol, palmarosa oil, and D-limonene in synergistic combination with an insecticidal soap having about 0.5% to about 2.0% by weight of potassium salts of fatty acids, such as oleic acid, which enhances the effectiveness of the composition sufficiently to render the otherwise relatively ineffective individual components functionally enhanced and quicker-acting, thereby improving both the mortality and the kill time. Among the deregulated essential oils, cedar oil and cornmint oil are particularly attractive because of their pleasant odors.

Still another object of this invention is the provision of an insecticidal composition comprising at least one or more essential oils, a synergist and pyrethrins, the combination of which reduces the quantity of the pyrethrins necessary to effect acceptable mortality rates in at least some insect populations, even further reducing the cost and dangers of using such materials by the general public. Compounds other than SLS and lecithin that can be used as synergists are insecticidally effective quantities of sodium dodecyl sulfate, potassium salts of fatty acids, ammonium salts of fatty acids, as well as plain fatty acids like hexadeconoic acid, lauric acid, myristic acid, and oleic acid.

Yet another object of this invention is to provide an insecticidal composition comprising at least one or more essential oils and an insecticidal soap composition such as the SAFER® Insect Killing Soap Concentrate, in combination with pyrethrins.

A further object of the present invention is the provision of a highly effective insecticidal composition, which may be sprayed in aerosol form from a standard pump dispenser or, which may incorporate a propellant such as carbon dioxide ($CO_2$), nitrogen ($N_2$) or the like, in a pressurized container of conventional design, so that the composition may be sprayed directly onto a crawling or flying insect pest.

Another object of this invention is the provision of an insecticidal composition of the type described incorporating mineral oil or other such material as a carrier oil to retain the essential oils on a contacted surface for residual killing power over an extended period of time.

These and other objects of the invention, as well as many of the attendant advantages thereof, will become more readily apparent when reference is made to the following detailed description of the preferred embodiments.

BRIEF DESCRIPTION OF THE DRAWINGS

FIG. 1 is a chart showing the test results of certain concentrations of mint oil in combination with various concentrations of synergists, pyrethrins, and insecticidal soap on killing German Cockroaches.

FIG. 2 is a chart showing the test results of certain concentrations of mint oil, D-limonene or palmarosa oil in combination with various concentrations of synergists, pyrethrins, and insecticidal soap on killing Carpenter Ants.

FIG. 3 is a chart showing the test results of certain concentrations of eugenol in combination with various concentrations of synergists, pyrethrins, and insecticidal soap on killing German Cockroaches.

FIG. 4 is a chart showing the test results of certain concentrations of thyme oil in combination with various concentrations of synergists, pyrethrins, and insecticidal soap on killing German Cockroaches.

FIG. 5 is a chart showing the test results of certain concentrations of mint oil, D-limonene and palmarosa oil in combination with various concentrations of synergists, pyrethrins, and insecticidal soap on killing German Cockroaches.

FIG. 6 is a chart showing the test results of certain concentrations of various essential oils in combination with various concentrations of pyrethrins, and insecticidal soap on killing Carpenter Ants.

FIG. 7 is a chart showing the test results of certain concentrations of D-limonene in combination with various concentrations of synergists, pyrethrins, and insecticidal soap on killing German Cockroaches.

DETAILED DESCRIPTION AND PREFERRED EMBODIMENTS

In describing a preferred embodiment of the invention specific terminology will be resorted to for the sake of clarity. However, the invention is not intended to be limited to the specific terms so selected, and it is to be understood that each specific term includes all technical equivalents which operate in a similar manner to accomplish a similar purpose.

It has previously been shown that the combination of certain essential oils and a synergist, such as SLS or lecithin, is an effective insecticidal composition in U.S. Pat. Nos. 5,998,484 and 6,548,085.

In its broadest aspects, the essential active ingredients in the compositions of the instant invention are any of the following: a) the combination of at least one or more essential oils and insecticidal soap; b) the combination of at least one or more essential oils, insecticidal soap and pyrethrins; c) the combination of at least one or more essential oils and pyrethrins; d) the combination of at least one or more essential oils, insecticidal soap and a synergist; e) the combination of at least one or more essential oils, insecticidal soap, pyrethrins and a synergist; and f) the combination of at least one or more essential oils, pyrethrins and a synergist. The active ingredients are preferably dissolved in an inert carrier such as water.

The essential oils which are useful in the present invention include cornmint (mint) oil, cedar oil, cinnamon oil, citronella oil, clove oil, corn oil, garlic oil, lemongrass oil, linseed oil, peppermint oil, rosemary oil, soybean oil, citrus oils such as orange oil, lemon oil, lime oil, grapefruit oil and tangerine oil, neem oil, thyme oil, eugenol, geraniol, palmarosa oil, and D-limonene.

Any suitable insecticidal soap can be used in the compositions of the present invention; however, SAFER® Brand Insect Killing Soap Concentrate is a preferred insecticidal soap. The SAFER® Brand Insect Killing Soap Concentrate includes 43.96% Emersol 213 (Oleic Acid), 5.56% potassium hydroxide, 35.61% denatured alcohol (SD3A or SDA 3C), and 14.87% water. This composition contains about 49.52% potassium salts of fatty acids by weight.

Any suitable pyrethrin concentrate, such as those commercially available on the market, can be used in the compositions of the present invention. In order to prevent the pyrethrins from breaking down, an antioxidant such as ethoxyquin, a tocopherol, or BHT is typically present in the pyrethrin concentrate, or otherwise should preferably be included in the insecticidal compositions. An alcohol is also preferably included, such as SD3A or SDA 3C, or other denatured alcohol, inasmuch as pyrethrins are not readily soluble in the water-based compositions of the present invention.

A material such as mineral oil may be incorporated into the composition as a carrier oil to provide residual killing power on surfaces for up to, as much as, four weeks or more. The essential oil is dissolved in the carrier oil and prevents the rather volatile essential oil from evaporating quickly. As a result, the insects come in contact with the carrier oil composition that will eventually kill them. Many other oils other than mineral oil are capable of performing the function of the carrier oil. Some examples are soybean oil, canola oil, corn oil, sunflower oil, neem oil, peanut oil, sesame oil, cottonseed oil, fish oil, olive oil, safflower oil, or castor oil. Obviously, some oils have characteristics that make them more or less suitable for certain applications based on odor, color, cost and availability.

The synergists which can be used in the compositions of the present invention include SLS, sodium dodecyl sulfate and lecithin.

The compositions of the present invention may be dispensed in a conventional manner, e.g., from a standard pump-spray container. Alternatively, and preferably, the aqueous insecticidal composition may be packaged in a pressurized container such as a conventional aerosol can or the like, utilizing an expandable gas, such as carbon dioxide ($CO_2$) as a propellant in a well-known manner. For optimum effectiveness, the insecticidal composition of this invention is sprayed directly on targeted crawling or flying insect pests in sufficient concentrations to cause death within seconds.

The compositions of the present invention are generally described as follows:

1) a composition comprising an insecticidal soap providing from about 0.5% to about 4.0% by weight of potassium salts of fatty acids to the overall composition, from about 0.25% to about 12% of one or more essential oils, and the balance water;

2) a composition comprising an insecticidal soap providing from about 0.5% to about 4.0% by weight of potassium salts of fatty acids to the overall composition, from about 0.25% to about 12% of one or more essential oils, from about 0.01% to 0.5% pyrethrins, and the balance water;

3) a composition comprising from about 0.25% to about 12% of one or more essential oils, from about 0.01% to 0.5% pyrethrins, and the balance water;

4) a composition comprising from about 0.25% to about 12% of one or more essential oils, an insecticidal soap providing from about 0.5% to about 4.0% by weight of potassium salts of fatty acids, and from 0.25% to about 5% of a synergist, and the balance water;

5) a composition comprising from about 0.25% to about 12% of one or more essential oils, an insecticidal soap providing from about 0.5% to about 4.0% by weight of potassium salts of fatty acids, from about 0.01% to 0.5% pyrethrins, and from about 0.25% to about 5% of a synergist, and the balance water; and 6) a composition comprising from about 0.25% to about 12% of one or more essential oils, from about 0.01% to about 0.5% pyrethrins, and from about 0.25% to about 5% of a synergist, and the balance water.

The above compositions may be combined with a carrier oil should such properties be desired in the composition for various applications. Preferably, the amount of carrier oil present in the composition can be in the range of about 3% to about 8% by weight of the carrier oil, such as mineral oil.

The testing described below establishes that insecticidal soap alone is less effective in killing the targeted insects. Further, in most instances, the tested essential oils alone either do not kill the targeted insects, or if they eventually kill some of the targeted insects, they generally require relatively high concentrations of the essential oil, and/or they are relatively slow-acting.

All treatments were dispensed using a hand pump trigger sprayer. When the insect pests track through, and come in contact with, previously sprayed product, the active ingredients remain on their bodies and they eventually die. Without the mineral oil, the composition dries, leaving no residue.

To evidence the unexpectedly improved nature of the results obtained using the synergistic insecticidal compositions of the instant invention, the foregoing tests were performed.

EXAMPLE 1

The following compositions were compared for effectiveness: a) the Victor® Poison Free Ant and Roach Killer formulation containing 4.0% mint oil as the sole active ingredient; b) Safer® brand Insect Killing Soap formulation providing a concentration of 2.0% potassium salts of fatty acids as the sole active ingredient; c) a formulation of 4.0% mint oil with 2.0% potassium salts of fatty acids; d) a formulation of 4.0% mint oil with 2.0% potassium salts of fatty acids and 3.0% lecithin; e) Victor® Poison Free Wasp & Hornet Killer formulation containing 8% mint oil with 1% SLS as the active ingredients; f) a formulation of 8% mint oil with 2% potassium salts of fatty acids; and g) a formulation of 8% mint oil with 2% potassium salts of fatty acids and 1% SLS. Previous experiments demonstrated that treatment of insects with 1% SLS alone did not kill insects within the 300 second time period used in testing (data not shown). All of the above formulations were tested using the American cockroach, *Periplaneta americana*, as the targeted insect.

American Cockroaches were obtained from a colony maintained at Woodstream Corporation in Lititz, Pa. PVC pipe was used to calm and confine the cockroaches prior to spraying. The PVC pipe is lined with Vaseline before introducing cockroaches to prevent escape.

The insecticidal soap used in all the following studies was Safer® Brand Insect Killing Soap Concentrate. The soap concentrate comprises 43.96% Emersol 213 (Oleic Acid), 5.56% potassium hydroxide, 35.61% denatured alcohol (SD3A or SDA 3C), and 14.87% water. This composition contains about 49.52% potassium salts of fatty acids by weight, and was used to formulate treatments containing 2.0% potassium salts of fatty acids by weight, and is described in U.S. Pat. Nos. 4,861,762, 4,983,591 and 5,047,424, previously incorporated herein by reference.

The experimental formulations were in the following percentages of the admixed components by weight:
Treatment 1: 2.0% Potassium Salts of Fatty Acids
   4.04% Safer® Brand Insect Killing Soap Concentrate
   95.96% water
Treatment 2: 4.0% Mint Oil with 2.0% Potassium Salts of Fatty Acids
   4.0% mint Oil
   5.0% mineral Oil
   4.04% Safer Insect Killing Soap Concentrate
   86.96% water Treatment 3: 4.0% Mint Oil with 3.0% Lecithin and 2.0% Potassium Salts of Fatty Acids
- 4.00% mint oil
- 5.00% mineral oil
- 3.00% lecithin
- 4.04% Safer® Brand Insect Killing Soap Concentrate
- 83.96% water Treatment 4: Victor® Poison Free Ant and Roach Insect Killer
- 4.0% mint oil
- 5.0% mineral oil
- 3.0% lecithin
- 88.0% water Treatment 5: 8% Mint Oil with 2% Potassium Salts of Fatty Acids
- 8% mint oil
- 4.04% Safer® Brand Insect Killing Soap Concentrate
- 87.96% water Treatment 6: 8% Mint Oil with 1% SLS and 2% Potassium Salts of Fatty Acids
- 8% mint Oil
- 1% SLS
- 4.04% Safer® Brand Insect Killing Soap Concentrate
- 86.96% water Treatment 7: Victor Poison Free Wasp & Hornet Killer
- 8% mint Oil
- 1% SLS
- 91% water The test formulations were applied to the American cockroach. Five replications were made for each test formulation, with one replication consisting of one (1) adult American cockroach. At the time of test initiation, one (1) American cockroach was placed into the PVC pipe within the testing arena. The cockroach was allowed to acclimate for approximately 1-2 minutes before being sprayed with the test formulation. The cockroach was sprayed from a distance of approximately 12 inches. Each cockroach was sprayed for 3 seconds within the PVC pipe. After spraying, the PVC pipe was removed and the kill time was recorded in seconds. The test was stopped when the insect was killed or 300 seconds had passed.

TABLE 1

Mean Kill Time in Seconds for American Cockroaches

| FORMULATION (% By. Wt) | Average Kill Time (seconds) |
|---|---|
| 2% potassium salts of fatty acids | 179.6 |
| 2.0% potassium salts of fatty acids + 4.0% mint oil | 265.8 |
| 2.0% potassium salts of fatty acids + 4.0% mint oil + 3% lecithin | 300 |
| 4% mint oil + 3% lecithin | 252 |
| 2% potassium salts of fatty acids + 8% mint oil | 253 |
| 2% potassium salts of fatty acids + 8% mint oil + 1% SLS | 135 |
| 8% mint oil + 1% SLS | 98.6 |

EXAMPLE 2

A study using the methodology of Example 1 was performed using German cockroaches (*Blatella garmanica*). Treatments 1, 2, and 3 consisted of aerosolized test material using carbon dioxide as the propellant. Aerosol cans were filled at LHB Industries (St. Louis, Mo.) per Woodstream specification. Treatment 4 was formulated in the Woodstream laboratory, placed into a bottle, and dispensed using a hand pump trigger sprayer.

The experimental formulations were in the following percentages of the admixed components by weight:

Treatment 1: Victor® Poison Free Ant and Roach Insect Killer
- 4.0% mint oil
- 5.0% mineral oil
- 3.0% lecithin
- 88.0% water Treatment 2: 4.0% Mint Oil with 3.0% Lecithin and 2.0% Potassium Salts of Fatty Acids
- 4.00% mint oil
- 5.00% mineral oil
- 3.00% lecithin
- 4.04% Safer Brand Insect Killing Soap Concentrate
- 83.96% water Treatment 3: 4.0% Mint Oil with 2.0% Potassium Salts of Fatty Acids
- 4.0% mint Oil
- 5.0% mineral Oil
- 4.04% Safer® Insect Killing Soap Concentrate
- 86.96% water Treatment 4: 2.0% Potassium Salts of Fatty Acids
- 4.04% Safer® Brand Insect Killing Soap Concentrate
- 95.96% water

TABLE 2

Mean Kill Time in Seconds for German Cockroaches

| FORMULATION (% By. Wt) | Average Kill Time (seconds) |
|---|---|
| 4.0% mint oil + 3.0% lecithin | 35.72 |
| 2.0% potassium salts of fatty acids + 4.0% mint oil + 3.0% lecithin | 33.81 |
| 2.0% potassium salts of fatty acids + 4.0% mint oil | 24.82 |
| 2.0% potassium salts of fatty acids | 38.36 |

EXAMPLE 3

A range of concentrations of pyrethrins from 0.01% to 0.5% by weight can be combined with 0.25% to 8% by weight of at least two essential oils such as mint and D-limonene or palmarosa oil and thyme oil. The formulation will include an anti-oxidant such as ethoxyquin, a tocopherol, or BHT to prevent the pyrethrins from breaking down. As pyrethrins are not readily water soluble, an alcohol may also be included, such as SD3A or SDA3C or other denatured alcohols in the composition to help solubilize the pyrethrins. Mineral oil or an equivalent substance can also be used at a concentration of about 5% by weight to allow the composition to remain on the surface for up to four weeks. The balance is water.

EXAMPLE 4

In another embodiment, two concentrations of insecticidal soap and pyrethrin are combined with several concentrations of at least two essential oils. The essential oil concentrations of the composition can range from 0.25% to 8.0% by weight. The concentration of pyrethrin in the contemplated composition is between about 0.01% to about 0.5% by weight as pyrethrin in this range has been shown to be effective in previous testing. As in Example 3, an anti-oxidant like ethoxyquin, a tocopherol, or BHT will be required to prevent the pyrethrin from breaking down. An alcohol may also be needed to solubilize the pyrethrin. The concentrations of soap in the contemplated composition are 0.5% and 2.0% by weight. Carrier oil or an equivalent substance can also be used at a concentration of up to about 5% by weight to allow the composition to remain on the surface for up to four weeks. The balance is water.

EXAMPLE 5

Tests were performed to determine the effectiveness of differing concentrations of mint oil with various combinations of lecithin, pyrethrins, potassium salts of fatty acids and SLS on the German Cockroach (*Biatella germanica*). The testing area, the PVC pipe and insects were the same as in Example 1.

The formulations of certain test components were as follows
   Safer® Brand Insecticidal Soap Concentrate: Contains 49.52% potassium salts of fatty acids by weight, as described above; and
   Pyganic MUP 20 (McLaughlin Gormley King Company, Golden Valley, Minn.): Contains 20% pyrethrins by weight.

The various test formulations, with percentages by weight, are set forth in the table comprising FIG. 1. Each formulation was applied to the cockroaches. Fifteen replications were made for each test formulation, with one adult male cockroach per replication. At the time of test initiation, 5 cockroaches are placed in the PVC pipe in the testing area. The cockroaches were allowed to acclimate for about 1-2 minutes before the test began. The cockroaches are then sprayed from a height of 12 inches into the pipe for about 3 seconds. The pipe is then removed and the kill time recorded in seconds for each cockroach. This procedure was repeated three times to obtain the fifteen replications.

The results of the experiments are also shown in FIG. 1. The control and pyrethrins combined with lecithin or 1% SLS only treatments were the least effective with kill times approaching five minutes. The fastest kill times were observed when the mint oil was combined with insecticidal soap and pyrethrins. Increasing the mint oil concentration resulted in faster kill times. Based on the results of this experiment, addition of pyrethrins to the composition comprising mint oil and insecticidal soap resulted in a synergistic effect, reducing kill times more than the combination of the mint oil and insecticidal soap without pyrethrins.

EXAMPLE 6

Tests were performed to determine the effectiveness of differing concentrations of mint oil, D-limonene, or palmarosa oil with various combinations of lecithin, pyrethrin, potassium salts of fatty acids and SLS on the Carpenter Ant (*Camponotus pennsylvanicus*). The testing area and the PVC pipe were the same as in Example 1. The ants were obtained from Carolina Biological Supply Company (Burlington, N.C.).

The formulations of the Safer® Brand Insecticidal Soap Concentrate and Pyganic MUP 20 were as described previously.

The various test formulations, with percentages by weight, are set forth in the table comprising FIG. 2. Each formulation was applied to the Carpenter Ants. Fifty replications were made for each test formulation with one replication consisting of one ant. At the time of test initiation, ten (10) ants were placed into the PVC pipe in the testing area as described previously. The ants were allowed to acclimate for 1-2 minutes before being sprayed with the test formulation. The ants were sprayed from a distance of about 12 inches for about 3 seconds within the pipe. The pipe is then removed and the kill time recorded in seconds for each ant. This procedure was repeated five times to obtain the fifty replications.

The results are also shown in FIG. 2. With the exception of the control and essential oils alone, all treatments were effective in killing the ants within five minutes. The fastest kill times occurred when the ants were treated with lecithin and essential oils, insecticidal soap and essential oils, and 1% SLS and pyrethrins and essential oils. The combination of either lecithin or insecticidal soap and essential oil resulted in a synergistic effect, reducing kill times more than the combined effect of each one separately. Addition of palmarosa oil reduced kill times more efficaciously than the mint oil or D-limonene.

EXAMPLE 7

Tests were performed to determine the effectiveness of differing concentrations of eugenol with various combinations of lecithin, pyrethrins, potassium salts of fatty acids and SLS on the German Cockroach (*Blatella germanica*). Eugenol is an aromatic chemical, fragrance and a spice that is derived from clove oil and cinnamon leaf. It has a characteristic spicy odor of clove. USP grade eugenol has uses in the food, dental and pharmaceutical industries. Eugenol is widely used in dentistry, due to its analgesic, antiseptic and balsamic qualities. The testing area, PVC pipe, insects, and testing procedures were the same as in Example 5. The formulations of Safer® Brand Insecticidal Soap Concentrate and Pyganic MUP 20 were as described previously.

The various test formulations, with percentages by weight, are set forth in the table comprising FIG. 3. The controls and treatments containing only pyrethrins combined with lecithin, or 1% SLS, were least effective in killing the cockroaches. The fastest kill times were observed when eugenol was combined with insecticidal soap, and soap plus pyrethrins. Increasing the concentration of eugenol decreased the kill times significantly. The data show a synergistic effect on reducing kill times of cockroaches when insecticidal soap at a concentration of either 0.5% or 2% by weight, is combined with eugenol at a concentration of either 1% or 4% by weight. The synergism is also seen when either is combined with 0.012% and 0.05% pyrethrins by weight.

EXAMPLE 8

Tests were performed to determine the effectiveness of differing concentrations of thyme oil with various combinations of lecithin, pyrethrins, potassium salts of fatty acids and SLS on the German Cockroach (*Blatella germanica*). The testing area, PVC pipe, insects and testing procedures were the same as in Example 5. The test formulations of Safer® Brand Insecticidal Soap Concentrate and Pyganic MUP 20 were as described previously.

The various test formulations, with percentages by weight, are set forth in the table comprising FIG. 4. The controls and treatments containing only pyrethrins combined with lecithin or 1% SLS were least effective in killing the cockroaches. The fastest kill times were observed when thyme oil was combined with insecticidal soap, or insecticidal soap plus pyrethrins. Increasing the concentration of thyme oil decreased the kill times significantly. The data show a synergistic effect on reducing kill times of cockroaches when the highest concentration of thyme oil (4% by weight), is combined with lecithin and pyrethrins, or when thyme oil is combined either with insecticidal soap or with insecticidal soap and pyrethrins.

EXAMPLE 9

Tests were performed to determine the effectiveness of differing concentrations of mint oil, D-Limonene or palmarosa oil with various combinations of lecithin, pyrethrins, potassium salts of fatty acids and SLS on the German Cockroach (*Blatella germanica*). The testing area, PVC pipe, insects and testing procedures were the same as in Example 5. The test formulations of Safer® Brand Insecticidal. Soap Concentrate and Pyganic MUP 20 were as described previously.

The various test formulations, with percentages by weight, are set forth in the table comprising FIG. 5. As shown in FIG. 5, most of the treatments were effective and resulted in kill times under 2 minutes. Typically, the higher concentrations of essential oils, by weight, resulted in reduced kill times, and palmarosa oil was shown to produce the fastest kill times.

Based on the results set forth in FIG. 5, it can be shown that synergy is occurring with the combination treatments of: lecithin and essential oils; pyrethrins, lecithin and essential oils; and pyrethrins, SLS and essential oils. The addition of mint oil and palmarosa oil significantly improved the efficacy of insecticidal soap. The addition of palmarosa oil significantly improved the efficacy of pyrethrins and insecticidal soap. Other combinations of essential oils and insecticidal soap, as well as insecticidal soap with pyrethrins did not result in statistically significant synergy.

EXAMPLE 10

This experiment was performed to compare the effectiveness of 0%, 0.25%, 1.0% and 4% by weight of mint Oil, D-limonene, thyme oil, eugenol, cedar oil, cinnamon oil, neem oil, and geraniol in combination with 0.012% pyrethrins and 1.0% potassium salts of fatty acids; 0.05% pyrethrins and 1.0% potassium salts of fatty acids; 0.05% pyrethrins and 2.0% potassium salts of fatty acids on the Carpenter Ant (*Camponotus pennsylvanicus*). The testing area PVC pipe, insects and testing procedures were the same as in Example 7. The test formulations of Safer® Brand Insecticidal Soap Concentrate and Pyganic MUP 20 were as described previously.

The various test formulations, with percentages by weight, are set forth in the table comprising FIG. 6. As shown FIG. 6, the shortest killing times were observed with the test combinations comprising the essential oils of D-limonene or geraniol. Killing time was reduced as the concentrations by weight of insecticidal soap and pyrethrins were increased. Killing time reduction was also observed as the concentrations of essential oils were increased.

Based on the results described in FIG. 6, it can be concluded that synergies are occurring between the test combinations of insecticidal soap, essential oils and pyrethrins.

EXAMPLE 11

This experiment was performed to compare the effectiveness of 0% and 1.0% mint oil, D-limonene, geraniol, and cinnamon oil in combination with 0.012% pyrethrins and 1.0% potassium salts of fatty acids; 0.03% pyrethrins and 1.0% potassium salts of fatty acids; 0.05% pyrethrins and 1.0% potassium salts of fatty acids on the House Fly (*Musca domestica*).

House Fly pupae were obtained from Carolina Biological and raised to adults in the Woodetream Laboratory. Screen Covered PVC Pipe was used to calm and confine the flies prior to spraying. The PVC pipe is covered with screen before introducing flies to prevent escape. The testing area and test formulations of Safer® Brand Insecticidal Soap Concentrate and Pyganic MUP 20 were as described previously.

The test formulations were applied to the flies. Fifteen replications were made for each test formulation with one replication consisting of (1) adult fly. At the time of test initiation, (5) flies were placed into the screened PVC pipe within the testing arena. The flies were allowed to acclimate approximately 1-2 minutes before being sprayed with the test formulation. The flies were sprayed from a distance of approximately 12 inches for about 3 seconds within the PVC pipe. After spraying, the PVC pipe was removed and the kill time recorded in seconds for each fly. This procedure was repeated five times to obtain the fifteen replications.

The various test formulations, with percentages by weight, are set forth in Table 3. The application of the test formulations immediately inhibited the flying ability of the test flies. The shortest kill times were observed with the combinations using D-Limonene or geraniol. Speed of kill was not increased as the percent of pyrethrins was increased. Based on these data it can be concluded that synergies are occurring between essential oils and potassium salts of fatty acids combined with pyrethrins. There were no significant differences in kill times with increased concentrations of pyrethrins indicating that synergy would be obtained with lower concentrations of pyrethrins with the same amount of essential oils.

TABLE 3

Mean Kill Time in Seconds for House Flies.

| Essential Oil | 0.012% Pyrethrin + 1.0% Soap | 0.03% Pyrethrin + 1.0% Soap | 0.05% Pyrethrin + 1.0% Soap |
|---|---|---|---|
| 0% Essential Oil | 41.993 | 44.013 | 53.267 |
| 1% Mint Oil | 34.653 | 35.04 | 32.48 |
| 1% D-Limonene | 45.273 | 21.747 | 62.887 |
| 1% Geraniol | 27.327 | 26.787 | 20.7 |
| 1% Cinnamon Oil | 30.5 | 34.533 | 45.367 |

EXPERIMENT 12

The purpose of this experiment was to determine the effectiveness of 0%, 0.25%, 1.0% and 4% of D-limonene by weight in combination with various concentrations of lecithin, potassium salts of fatty acids, SLS, and pyrethrins, on the German Cockroach (*Blatella germanica*). The testing area, PVC pipe, insects and test procedures were the same as in Example 5. The test formulations of Safer® Brand Insecticidal Soap Concentrate and Pyganic MUP 20 were as described previously.

The various test formulations, with percentages by weight are set forth in FIG. 7. The results of the experiments show that the water treatments, and treatment combinations containing only pyrethrins combined with lecithin or SLS, were least effective, with kill times approaching or exceeding 5 minutes. The fastest kill times were observed when D-limonene was combined with either insecticidal soap, or insecticidal soap and pyrethrins. As was expected, increasing the concentration of D-limonene reduced the killing times. Treatments of insecticidal soap and insecticidal soap combined with pyrethrins, resulted in faster kill times for the cockroaches, than treatments containing pyrethrins combined with lecithin or SLS. These observed differences were consistent even with the addition of D-limonene.

Essential oils of the present invention may be used in combination with insecticidal soap and pyrethrins to create an insecticidal composition that will result in a synergistic reduction of killing times for various insects. For example, cedar oil is expected to show synergistic results with similar levels of sodium lauryl sulfate as discussed above at levels of cedar oil from about 0.01 to 30%, with a preferred composition comprising from about 0.5 to 10% cedar oil; for clove oil, the broad range would be from about 0.01 to 30%, with a preferred range of from about 1 to 20%; for garlic oil, the broad range would be from about 0.1 to 30%, with a preferred range of from about 1 to 20%; for lemongrass oil, the broad range would be from about 0.01 to 20%, with a preferred range of from about 0.5 to 5%; for linseed oil, the broad range would be from about 0.01 to 30%, with a preferred range of from about 1 to 20%; for rosemary oil, the broad range would be from about 0.01 to 30%, with a preferred range of from about 1 to 30%; for soybean oil the broad range would be from about 0.01 to 80%, with a preferred range of from about 1 to 30%; and for thyme oil, the broad range would be from about 0.01 to 30%, with a preferred range of from about 0.5 to 10%.

Having described the invention, many modifications thereto will become apparent to those skilled in the art to which it pertains without deviation from the spirit of the invention as defined by the scope of the appended claims.

The invention claimed is:

1. An insecticidal composition comprising neem oil, soap, pyrethrins, and an antioxidant compound selected from the group consisting of ethoxyquin, a tocopherol, and BHT, wherein the composition is sprayable.

2. The insecticidal composition of claim 1, wherein the soap comprises potassium salts of fatty acids.

3. The insecticidal composition of claim 1, wherein the amount of neem oil is about 0.25% to about 12% by weight, the amount of soap is about 0.5% to about 4% by weight, the amount of pyrethrins is about 0.01% to about 0.5% by weight, and the remainder water and the antioxidant.

4. The insecticidal composition of claim 3, further comprising a carrier oil.

5. An insecticidal composition comprising neem oil, soap, pyrethrins, an antioxidant selected from the group consisting of ethoxyquin, a tocopherol, and BHT, and a synergist, wherein the composition is sprayable.

6. The insecticidal composition of claim 5, wherein the soap comprises potassium salts of fatty acids.

7. The insecticidal composition of claim 5, wherein said synergist is sodium lauryl sulfate, sodium dodecyl sulfate, or lecithin.

8. The insecticidal composition of claim 6, wherein the amount of neem oil is about 0.25% to about 12% by weight, the amount of pyrethrins is about 0.01% to about 0.5% by weight, the amount of potassium salts of fatty acids is about 0.5% to about 4% by weight, the amount of synergist is about 0.25% to about 5% by weight, and the remainder water and the antioxidant.

9. The insecticidal composition of claim 8, further comprising a carrier oil.

10. The insecticidal composition of claim 3, wherein said soap is an insecticidal soap containing oleic acid and denatured alcohol.

11. The insecticidal composition of claim 3, wherein said pyrethrins derive from a pyrethrin concentrate including an alcohol to solubilize the pyrethrins.

12. A method of killing one or more insects comprising spraying the composition of claim 1 onto one or more insects.

13. The method of claim 12, wherein the insecticidal composition further comprises an essential oil selected from the group consisting of: cornmint oil, cedar oil, cinnamon oil, citronella oil, clove oil, corn oil, garlic oil, lemongrass oil, linseed oil, peppermint oil, rosemary oil, soybean oil, thyme oil, orange oil, lemon oil, lime oil, grapefruit oil, tangerine oil, D-limonene, eugenol, geraniol, palmarosa oil, and mixtures thereof.

14. The method of claim 13, wherein the amount of neem oil is about 0.25% to about 12% by weight, the amount of soap is about 0.5% to about 4% by weight, the amount of pyrethrins is about 0.01% to about 0.5% by weight, and the remainder water and the antioxidant.

15. The method of claim 14, wherein the insecticidal composition further comprises an essential oil selected from the group consisting of D-limonene and palmarosa oil.

16. A method of killing one or more insects comprising spraying the composition of claim 5 onto one or more insects.

17. The insecticidal composition of claim 1, comprising neem oil, soap, pyrethrins, and ethoxyquin.

18. The insecticidal composition according to claim 1, wherein the antioxidant agent is ethoxyquin.

19. The insecticidal composition according to claim 5, wherein the antioxidant agent is ethoxyquin.

* * * * *